United States Patent
Neuba et al.

(10) Patent No.: US 11,529,304 B2
(45) Date of Patent: Dec. 20, 2022

(54) METHOD FOR DYEING KERATIN MATERIAL BY MEANS OF A DYEING AGENT AND AN ACIDIC POSTTREATMENT AGENT

(71) Applicant: Henkel AG & Co. KGaA, Duesseldorf (DE)

(72) Inventors: Costanze Neuba, Grevenbroich (DE); Sandra Hilbig, Bochum (DE); Daniela Kessler-Becker, Leverkusen (DE); Torsten Lechner, Langenfeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/415,625

(22) PCT Filed: Sep. 25, 2019

(86) PCT No.: PCT/EP2019/075846
§ 371 (c)(1),
(2) Date: Jun. 17, 2021

(87) PCT Pub. No.: WO2020/126137
PCT Pub. Date: Jun. 25, 2020

(65) Prior Publication Data
US 2022/0062156 A1    Mar. 3, 2022

(30) Foreign Application Priority Data
Dec. 18, 2018 (DE) ............ 10 2018 222 022.0

(51) Int. Cl.
*A61Q 5/10* (2006.01)
*A61K 8/898* (2006.01)
*A61K 8/19* (2006.01)
*A61K 8/25* (2006.01)
*A61K 8/34* (2006.01)
*A61K 8/362* (2006.01)

(52) U.S. Cl.
CPC ............... *A61K 8/898* (2013.01); *A61K 8/19* (2013.01); *A61K 8/25* (2013.01); *A61K 8/342* (2013.01); *A61K 8/362* (2013.01); *A61Q 5/10* (2013.01); *A61K 2800/43* (2013.01); *A61K 2800/438* (2013.01); *A61K 2800/4324* (2013.01); *A61K 2800/88* (2013.01)

(58) Field of Classification Search
CPC .... A61Q 5/10; A61K 8/19; A61K 2800/4324; A61K 2800/88; A61K 2800/884; A61K 2800/87; A61K 2800/43; A61K 8/898; A61K 8/25; A61K 8/585; A61K 8/342; A61K 8/362; A61K 2800/438
USPC .......................................................... 8/405
See application file for complete search history.

(56) References Cited

U.S. PATENT DOCUMENTS

| | | | |
|---|---|---|---|
| 10,653,598 B2 | 5/2020 | Schoepgens et al. | |
| 2010/0083446 A1* | 4/2010 | Brun ..................... | A61K 8/891 8/405 |
| 2013/0344021 A1* | 12/2013 | Meder .................... | A61Q 5/004 424/70.122 |
| 2017/0172901 A1* | 6/2017 | Kerl ....................... | A61K 8/22 |
| 2017/0347771 A1 | 12/2017 | Schoepgens et al. | |

FOREIGN PATENT DOCUMENTS

| CN | 108468232 A | 8/2018 |
|---|---|---|
| DE | 102013226102 A1 | 6/2015 |
| DE | 102015222214 A1 | 5/2017 |
| DE | 102016209981 A1 | 12/2017 |

OTHER PUBLICATIONS

STIC Search Report dated Jan. 12, 2022.*
EPO, International Search Report issued in International Application No. PCT/EP2019/075846, dated Nov. 11, 2019.

* cited by examiner

*Primary Examiner* — Eisa B Elhilo
(74) *Attorney, Agent, or Firm* — Lorenz & Kopf, LLP

(57) ABSTRACT

A process and a kit-of-parts are provided for dyeing keratinous material, in particular human hair. The process includes applying a coloring agent (a) to the keratinous material, the agent (a) comprising (a1) at least one amino-functionalized silicone polymer, (a2) at least one color-imparting compound, and (a3) at least one nonionic surfactant. The process further includes applying a post-treatment agent (b) to the keratinous material, the agent (b) comprising (b1) at least one acid.

19 Claims, No Drawings

METHOD FOR DYEING KERATIN MATERIAL BY MEANS OF A DYEING AGENT AND AN ACIDIC POSTTREATMENT AGENT

CROSS-REFERENCE TO RELATED APPLICATION

This application is a U.S. National-Stage entry under 35 U.S.C. § 371 based on International Application No. PCT/EP2019/075846, filed Sep. 25, 2019, which was published under PCT Article 21(2) and which claims priority to German Application No. 10 2018 222 022.0, filed Dec. 18, 2018, which are all hereby incorporated in their entirety by reference.

TECHNICAL FIELD

The subject of the present application is a process for dyeing keratinous material, in particular human hair, which comprises the application of at least two different agents (a) and (b). The agent (a) comprises at least one amino-functionalized silicone polymer (a1), at least one colorant compound (a2), and at least one nonionic surfactant (a3). The agent (b) is a post-treatment agent containing at least one acid (b1).

BACKGROUND

The second subject-matter of this application is a multi-component packaging unit (kit-of-parts) for coloring keratinous material, in particular human hair, which comprises the agents (a) and (b) separately packaged in two different containers.

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

BRIEF SUMMARY

The purpose of the present disclosure was to provide a dyeing system with fastness properties comparable to those of oxidative dyeing. However, the oxidation dye precursors normally used for this purpose should not be used. A technology was sought that would make it possible to fix the coloring compounds (such as pigments) known from the state of the art in an extremely durable way to the hair. When using the agents in a dyeing process, intensive dyeing results should be obtained, especially in fashionable shades. Focus was placed on creating fashionable shades with a strong, long-lasting sheen Surprisingly, it has now been found that the task can be excellently solved if keratinous materials, in particular hair, are colored by a process in which at least two agents (a) and (b) are applied to the keratinous materials (to the hair). Here, the agent (a) comprises at least one amino-functionalized silicone polymer (a1), at least one colorant compound (a2) and at least one nonionic surfactant (a3). The agent (b) represents an acidic post-treatment agent and contains at least one acid (b1). When both agents (a) and (b) were used in a dyeing process, it was possible to dye keratinous materials with high color intensity, which were exemplified by a particularly strong gloss that lasted even over several washes.

In an embodiment, a process is provided for dyeing keratinous material, in particular human hair. The process includes applying a coloring agent (a) to the keratinous material, the agent (a) comprising (a1) at least one amino-functionalized silicone polymer, (a2) at least one color-imparting compound, and (a3) at least one nonionic surfactant. The process further includes applying a post-treatment agent (b) to the keratinous material, the agent (b) comprising (b 1) at least one acid.

In another embodiment, a kit-of-parts for dyeing keratinous material is provided. The kit-of-parts includes, separately packaged, a first container and a second container. The first container includes a coloring agent (a), the agent (a) comprising (a1) at least one amino-functionalized silicone polymer, (a2) at least one color-imparting compound, and (a3) at least one nonionic surfactant. The second container includes a second container comprising an agent (b), wherein the agent (b) comprises (b1) at least one acid.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is a method for coloring keratinous material, in particular human hair, comprising the following steps:
applying a coloring agent (a) to the keratinous material, the agent (a) comprising:
(a1) at least one amino-functionalized silicone polymer,
(a2) at least one color-imparting compound, and
(a3) at least one nonionic surfactant, and applying a post-treatment agent (b) to the keratinous material, the agent (b) comprising:
(b1) at least one acid.

In the work leading to the present disclosure, it has been shown that successive application of colorant (a) and after treatment agent (b) results in colored keratinous material exemplified by high color intensities and particularly long-lasting gloss.

Without being limited to this theory, it is believed that the amino-functionalized silicone polymer (a1) contained in the colorant (a) forms adhesive bonds with the keratin material, which initially fix the amino silicone (a1) to the keratin material. The colorant compounds (a2) are incorporated into or onto the aminosilicone (a1) and are thus also immobilized on the outside of the keratin material.

The adhesive bonds between amino-functionalized silicone polymer (a1) and keratin are presumably based on electrostatic interactions formed between the positively charged amino groups of the silicone polymer (a1) and negative charges on the keratin material.

Surprisingly, it was observed that the color-imparting compounds (a2) attach to the latter or form a common layer with the amino silicone (a1) when used simultaneously. This joint layer formation of (a1) and (a2) means that colorations with high color intensity can be obtained, even without the need for diffusion of the colorant compound into the hair fiber. In an unpredictable way, the layer formed in this way was exemplified by an extremely high gloss, allowing the creation of fashionable, highly glossy shades. In this context, it was also found that the observed hair gloss was particularly strong when mainly nonionic ingredients were used in agent (a). For this reason, the agent (a) further comprises at least one nonionic surfactant (a3).

Furthermore, it was found that when aminosilicone (a1) and colorant compound (a2) were deposited together, very stable layers could be formed, especially when optimum pH values were selected during the application process. Particularly resistant coatings could be obtained if (a1) and (a2) were first applied to the keratin materials in a neutral to basic environment, and the pH was subsequently lowered by applying an acidic post-treatment agent. Keratin materials treated in this way retained their gloss even after several washes (such as hair washes).

Keratinic Material

Keratinous material includes hair, skin, nails (such as fingernails and/or toenails). Wool, furs, and feathers also fall under the definition of keratinous material. Preferably, keratinous material is understood to be human hair, human skin, and human nails, especially fingernails and toenails. Keratinous material is understood to be human hair.

Agent (a) and (b)

In the procedure as contemplated herein, agents (a) and (b) are applied to the keratinous material, in particular human hair. In exemplary embodiments, (a) and (b) are different.

In other words, a first subject of the present disclosure is a process for dyeing keratinous material, in particular human hair, comprising the following steps:

Application of a coloring agent (a) to the keratinous material, said agent (a) comprising:
(a1) at least one amino-functionalized silicone polymer, and
(a2) at least one color-imparting compound, and
(a3) at least one nonionic surfactant, and Application of a post-treatment agent (b) to the keratinous material, the agent (b) comprising:
(b1) at least one acid, where the agents (a) and (b) are different from each other.

Amino Functionalized Silicone Polymer (a1) in the Agent (a)

As the first ingredient (a1) essential to the present disclosure, the agent (a) comprises at least one amino-functionalized silicone polymer. The amino-functionalized silicone polymer may alternatively be referred to as aminosilicone or amodimethicone.

Silicone polymers are generally macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than $10^7$ g/mol, preferably not more than $10^6$ g/mol, and particularly preferably not more than $10^5$ g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized polydimethylsiloxane which carries at least one structural unit with an amino group. Preferably, the amino-functionalized silicone polymer carries multiple structural units, each having at least one amino group. An amino group is understood to mean a primary amino group, a secondary amino group, and a tertiary amino group. All these amino groups can be protonated in the acidic environment and are then present in their cationic form. In neutral to basic environments, these amino groups are uncharged.

In principle, good effects could be obtained with amino-functionalized silicone polymers (a1) if they carry at least one primary, at least one secondary, and/or at least one tertiary amino group. However, colorations with the best color intensity and the highest gloss were observed when an amino-functionalized silicone polymer (a1) was used in agent (a), which contains at least one secondary amino group.

In a very particularly preferred embodiment, a process as contemplated herein is exemplified in that the agent (a) comprises at least one amino-functionalized silicone polymer (a1) having at least one secondary amino group.

The secondary amino group(s) may be located at various positions on the amino-functionalized silicone polymer. Particularly good effects were found when an amino-functionalized silicone polymer (a1) was used that has at least one, preferably several, structural units of the formula (Si-Amino)

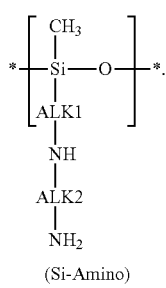

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, a process as contemplated herein is exemplified in that the agent (a) comprises at least one amino-functionalized silicone polymer (a1) comprising at least one structural unit of the formula (Si-Amino),

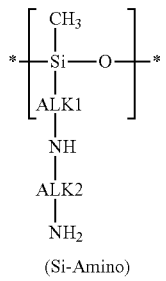

(Si-Amino)

Where ALK1 and ALK2 independently of one another represent a linear or branched, divalent $C_1$-$C_{20}$ alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A divalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear divalent $C_1$-$C_{20}$ alkylene group include the methylene group (—$CH_2$), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In another particularly preferred embodiment, the structural units of the formula (Si-Amino) represent repeat units in the amino-functionalized silicone polymer (a1), so that the silicone polymer comprises multiple structural units of the formula (Si-Amino)

Particularly well-suited amino-functionalized silicone polymers (a1) with at least one secondary amino group are listed below.

Colorations with the best intensities and the highest gloss could be obtained if, in the process as contemplated herein, at least one agent (a) containing at least one amino-functionalized silicone polymer (a1) comprising structural units of the formula (Si—I) and of the formula (Si—II) was applied to the keratinous material

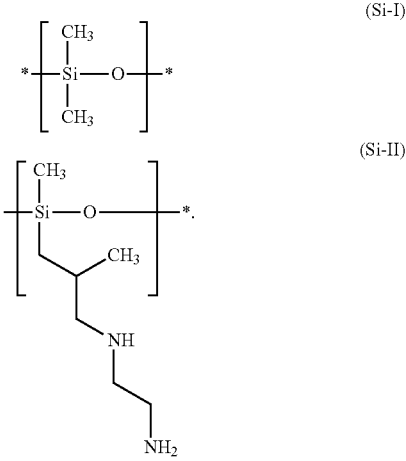

In a further quite particularly preferred embodiment, a process as contemplated herein is exemplified in that the agent (a) contains at least one amino-functionalized silicone polymer (a1) which comprises structural units of the formula (Si-I) and of the formula (Si-II)

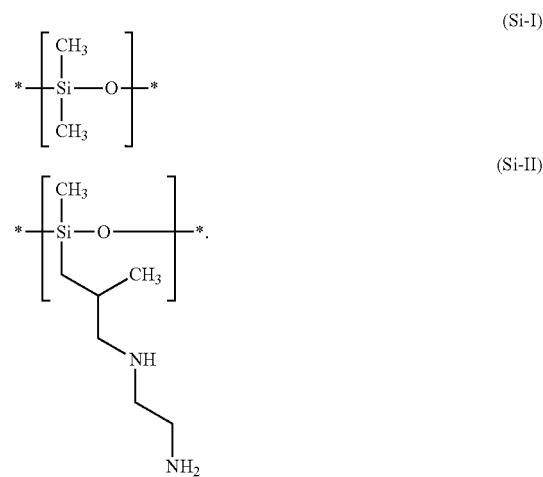

A corresponding amino-functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8.

In the context of a further preferred embodiment, a process as contemplated herein is exemplified by the application of an agent (a) to the keratinous material, the agent (a)

comprising at least one amino-functional silicone polymer (a1) of the formula of formula (Si-III),

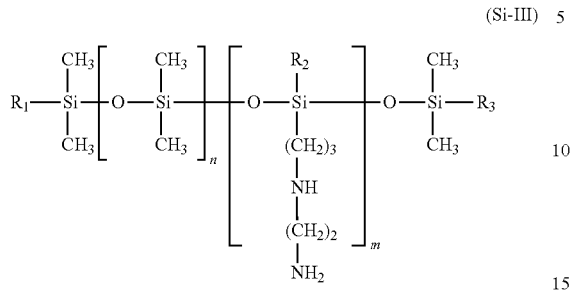

(Si-III)

where
- m and n mean numbers chosen so that the sum (n+m) is in the range 1 to 1000,
- n is a number in the range from 0 to 999 and m is a number in the range from 1 to 1000,
- R1, R2 and R3, which are the same or different, denote a hydroxy group or a C1-4 alkoxy group,
- wherein at least one of R1 to R3 represents a hydroxy group;

Further methods preferred as contemplated herein are exemplified by the application of an agent (a) to the keratinous material, the agent (a) comprising at least amino-functional silicone polymer (a1) of the formula of formula (Si-IV),

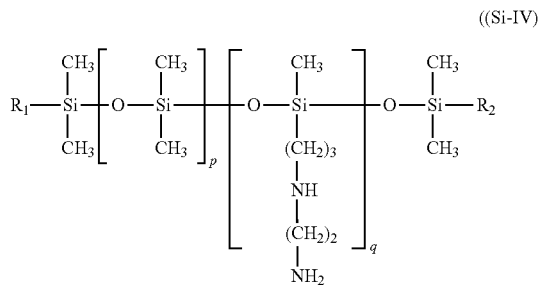

((Si-IV)

wherein
- p and q mean numbers chosen so that the sum (p+q) is in the range from about 1 to about 1000,
- p is a number in the range from about 0 to about 999 and q is a number in the range from about 1 to about 1000,
- R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si-III) and (Si-IV), not every R1—Si(CH$_3$)$_2$ group is necessarily bonded to an —[O—Si(CH$_3$)$_2$]— grouping.

Processes as contemplated herein in which an agent (a) containing at least one amino-functional silicone polymer (a1) of the formula of the formula (Si-V) is applied to the keratin fibers have also proved to be particularly effective with respect to the desired effects

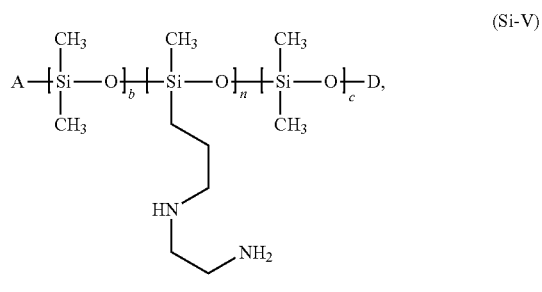

(Si-V)

wherein
A represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
b, n, and c stand for integers between 0 and 1000,
with the specifications
n>0 and b+c>0
at least one of the conditions A=—OH or D=—H is fulfilled.

In the above formula (Si-V), the individual siloxane units are statistically distributed with the indices b, c, and n, i.e., they do not necessarily have to be block copolymers.

The agent (a) may further comprise one or more different amino-functionalized silicone polymers represented by the formula (Si-VI)

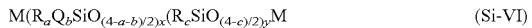

M(R$_a$Q$_b$SiO$_{(4-a-b)/2}$)$_x$(R$_c$SiO$_{(4-c)/2}$)$_y$M   (Si-VI)

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from about 1 to about 2000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl, and the like; alkenyl radicals, such as vinyl, halovinyl, alkylvinyl, allyl, haloallyl, alkylallyl; cycloalkyl radicals, such as cyclobutyl, cyclopentyl, cyclohexyl, and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl, and the like, and sulfur-containing radicals, such as mercaptoethyl, mercaptopropyl, mercaptohexyl, mercaptophenyl, and the like; preferably R is an alkyl radical containing from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional residue containing at least one amino functional group. One possible formula for Z is NH(CH$_2$)$_z$NH$_2$, where z is 1 or more. Another possible formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ residue. Another possible formula for Z is —N(CH$_2$)$_z$(CH$_2$)$_{zz}$NX$_2$ or —NX$_2$, wherein each X of X$_2$ is independently selected from the group consisting of hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$ SiO$_{(4-a-b)/2}$ units to R$_c$SiO$_{(4-c)/2}$ units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the agent (a) contains an amino-functional silicone polymer of formula (Si-VII)

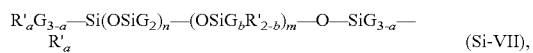

(Si-VII), wherein means:

G is —H, a phenyl group, OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, CH(CH$_3$)CH$_2$CH$_3$, —O—C(CH$_3$)$_3$, —C(CH$_3$)$_3$;

a stands for a number between 0 and 3, especially 0;

b stands for a number between 0 and 1, especially 1;

m and n are numbers whose sum (m+n) is between about 1 and about 2000, preferably between about 50 and about 150, where n preferably assumes values from about 0 to about 1999 and from about 49 to about 149 and m preferably assumes values from 1 to 2000, from about 1 to about 10, R' is a monovalent radical selected from

-Q-N(R")—CH$_2$—CH$_2$—N(R")$_2$

-Q-N(R")$_2$

-Q-N$^+$(R")$_3$A$^-$

-Q-N$^+$H(R")$_2$ A$^-$

-Q-N$^+$H$_2$(R")A$^-$

-Q-N(R")—CH$_2$—CH$_2$—N$^+$R"H$_2$A$^-$, where each Q is a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—, R" represents identical or different radicals selected from the group consisting of —H, -phenyl, -benzyl, —CH$_2$—CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In the context of a further preferred embodiment, a process as contemplated herein is exemplified by the application of an agent (a) to the keratinous material, the agent (a) comprising at least one amino-functional silicone polymer (a1) of the formula (Si-VIIa),

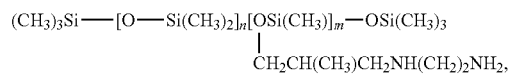

(Si-VIIa)

wherein m and n are numbers whose sum (m+n) is between about 1 and about 2000, preferably between about 50 and about 150, n is preferably a value from about 0 to about 1999, such as from about 49 to about 149, and m is preferably a value from about 1 to about 2000, such as from about 1 to about 10.

According to the INCI declaration, these silicones are called trimethylsilylamodimethicones.

In another preferred embodiment, a method as contemplated herein is exemplified by the application of an agent (a) to the keratinous material, said agent (a) comprising at least one amino-functional silicone polymer of formula (Si-VIIb)

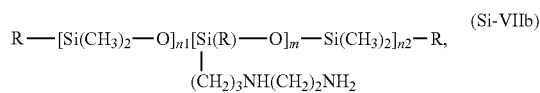

(Si-VIIb)

in which R represents —OH, —O—CH$_3$ or a —CH$_3$ group, and m, n1 and n2 are numbers whose sum (m+n1+n2) is between about 1 and about 2000, preferably between about 50 and about 150, the sum (n1+n2) is preferably a value from about 0 to about 1999, such as from about 49 to about 149, and m is preferably a value from about 1 to about 2000, such as from about 1 to about 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above 0.25 meq/g, preferably above 0.3 meq/g, such as above 0.4 meq/g. The amine number represents the milliequivalents of amine per gram of the amino-functional silicone. It can be determined by titration and also expressed in the unit mg KOH/g.

Furthermore, agents (a) which contained a special 4-morpholinomethyl-substituted silicone polymer (a1) are also suitable for use in the process as contemplated herein. This amino-functionalized silicone polymer comprises structural units of the formulae (SI-VIII) and of the formula (Si-IX)

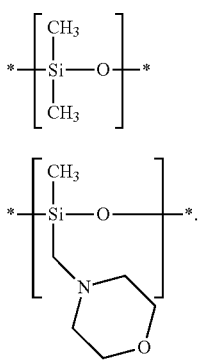

Corresponding 4-morpholinomethyl-substituted silicone polymers are described below.

A suitable amino-functionalized silicone polymer in this context is known as amodimethicone/morpholinomethyl silsesquioxane copolymer and is commercially available in the form of the raw material Belsil ADM 8301 E from Wacker.

As a 4-morpholinomethyl-substituted silicone, for example, a silicone can be used which has structural units of the formulae (Si-VIII), (Si-IX), and (Si-X)

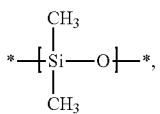

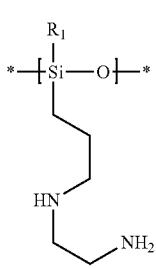

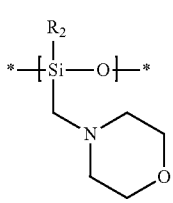

in which
R1 is —CH$_3$, —OH, —OCH$_3$, —O—CH$_2$CH$_3$, —O—CH$_2$CH$_2$CH$_3$, or —O—CH(CH$_3$)$_2$; and
R2 is —CH$_3$, —OH, or —OCH$_3$.

Particularly preferred compositions (a) as contemplated herein comprise at least one 4-morpholinomethyl-substituted silicone of the formula (Si-XI)

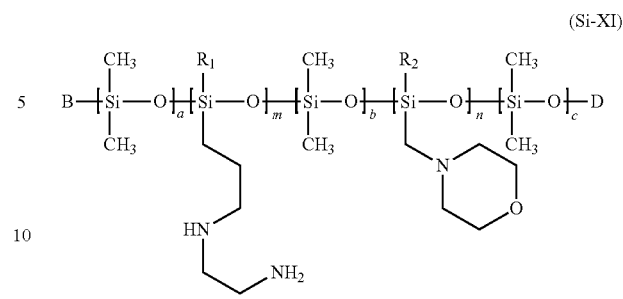

wherein
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si(CH$_3$)$_2$OH, or —O—Si(CH$_3$)$_2$OCH$_3$,
D represents a group —H, —Si(CH$_3$)$_3$, —Si(CH$_3$)$_2$OH, or —Si(CH$_3$)$_2$OCH$_3$,
a, b, and c stand independently for integers from 0 to 1000, with the condition that a+b+c 0, and
m and n independently of each other stand for integers from about 1 to about 1000, with the proviso that
  at least one of the conditions B=—OH or D=—H is fulfilled,
  the units a, b, c, m, and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0, and in particularly preferred formulas (Si-VI), a>0 and c>0, i.e., the terminal grouping B or D is preferably attached to a dimethylsiloxy grouping. Also, in formula (Si-VI), the siloxane units a, b, c, m, and n are preferably statistically distributed.

The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH. These silicones lead to exorbitant improvements in the hair properties of the hair treated with the agents of the present disclosure, and to a seriously improved protection in oxidative treatment.

To produce particularly resistant films, the agent (a) contains the amino-functionalized silicone polymer(s) (a2), preferably in specific ranges of amounts.

Particularly robust films were obtained when an agent (a) was used in the process as contemplated herein which contains—based on the total weight of the agent (a)—one or more silicone polymers in a total amount of from about 0.1 to about 8.0% by weight, preferably from about 0.2 to about 6.0% by weight, more preferably from about 0.5 to about 5.0% by weight, and very particularly preferably from about 1.0 to about 3.5% by weight.

In another preferred embodiment, a process as contemplated herein is exemplified in that the agent (a) contains— based on the total weight of the agent (a)—one or more amino-functionalized silicone polymers in a total amount of from about 0.1 to about 8.0% by weight, preferably from about 0.2 to about 6.0% by weight, more preferably from about 0.5 to about 5.0% by weight, and very preferably from about 1.0 to about 3.5% by weight.

Colorant Compound (a2) in the Medium (a)

As a second constituent essential to the present disclosure, the agent (a) used in the process as contemplated herein contains at least one color-imparting compound (a2).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a process as contemplated herein is exemplified in that the agent (a) comprises at least one colorant compound (a2) from the group consisting of pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stirrer is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent (a) as contemplated herein exemplified contains at least one colorant compound (a2) from the group consisting of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red, as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510), and/or carmine (cochineal).

Colored pearlescent pigments are particularly preferred as contemplated herein. These are usually mica- and/or mica-based and can be coated with one or more metal oxides. Mica belongs to the layer silicates. The most important representatives of these silicates are muscovite, phlogopite, paragonite, biotite, lepidolite, and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein is exemplified in that the agent (a) comprises at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments, and/or from colored mica- or mica-based pigments coated with at least one metal oxide and/or a metal oxychloride.

By using pearlescent pigments or effect pigments, colorations with a particularly high gloss can be achieved, so the use of these pigments is especially preferred.

In another very particularly preferred embodiment, a process as contemplated herein is exemplified in that the agent (a) comprises at least one colorant compound (a2) from the group of pigments selected from mica- or mica-based pigments which are reacted with one or more metal oxides from the group including titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288), and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:

Colorona Copper, Merck, MICA, CI 77491 (IRON OXIDES),
Colorona Passion Orange, Merck, Mica, CI 77491 (Iron Oxides), Alumina,
Colorona Patina Silver, Merck, MICA, CI 77499 (IRON OXIDES), CI 77891 (TITANIUM DIOXIDE),
Colorona RY, Merck, CI 77891 (TITANIUM DIOXIDE), MICA, CI 75470 (CARMINE),
Colorona Oriental Beige, Merck, MICA, CI 77891 (TITANIUM DIOXIDE), CI 77491 (IRON OXIDES),
Colorona Dark Blue, Merck, MICA, TITANIUM DIOXIDE, FERRIC FERROCYANIDE,
Colorona Chameleon, Merck, CI 77491 (IRON OXIDES), MICA,
Colorona Aborigine Amber, Merck, MICA, CI 77499 (IRON OXIDES), CI 77891 (TITANIUM DIOXIDE),
Colorona Blackstar Blue, Merck, CI 77499 (IRON OXIDES), MICA,
Colorona Patagonian Purple, Merck, MICA, CI 77491 (IRON OXIDES), CI 77891 (TITANIUM DIOXIDE), CI 77510 (FERRIC FERROCYANIDE),
Colorona Red Brown, Merck, MICA, CI 77491 (IRON OXIDES), CI 77891 (TITANIUM DIOXIDE),
Colorona Russet, Merck, CI 77491 (TITANIUM DIOXIDE), MICA, CI 77891 (IRON OXIDES), Colorona Imperial Red, Merck, MICA, TITANIUM DIOXIDE (CI 77891), D&C RED NO. 30 (CI 73360),
Colorona Majestic Green, Merck, CI 77891 (TITANIUM DIOXIDE), MICA, CI 77288 (CHROMIUM OXIDE GREENS),
Colorona Light Blue, Merck, MICA, TITANIUM DIOXIDE (CI 77891), FERRIC FERROCYANIDE (CI 77510),
Colorona Red Gold, Merck, MICA, CI 77891 (TITANIUM DIOXIDE), CI 77491 (IRON OXIDES),
Colorona Gold Plus MP 25, Merck, MICA, TITANIUM DIOXIDE (CI 77891), IRON OXIDES (CI 77491),
Colorona Carmine Red, Merck, MICA, TITANIUM DIOXIDE, CARMINE,
Colorona Blackstar Green, Merck, MICA, CI 77499 (IRON OXIDES),
Colorona Bordeaux, Merck, MICA, CI 77491 (IRON OXIDES),
Colorona Bronze, Merck, MICA, CI 77491 (IRON OXIDES),
Colorona Bronze Fine, Merck, MICA, CI 77491 (IRON OXIDES),
Colorona Fine Gold MP 20, Merck, MICA, CI 77891 (TITANIUM DIOXIDE), CI 77491 (IRON OXIDES),
Colorona Sienna Fine, Merck, MICA, CI 77491 (IRON OXIDES), MICA,
Colorona Sienna, Merck, MICA, CI 77491 (IRON OXIDES),
Colorona Precious Gold, Merck, Mica, CI 77891 (Titanium dioxide), Silica, CI 77491(Iron oxides), Tin oxide,
Colorona Sun Gold Sparkle MP 29, Merck, MICA, TITANIUM DIOXIDE, IRON OXIDES, MICA, CI 77891, CI 77491 (EU),
Colorona Mica Black, Merck, CI 77499 (Iron oxides), Mica, CI 77891 (Titanium dioxide),
Colorona Bright Gold, Merck, Mica, CI 77891 (Titanium dioxide), CI 77491(Iron oxides),
Colorona Blackstar Gold, Merck, MICA, CI 77499 (IRON OXIDES).
Other particularly preferred color pigments with the trade name Xirona® are for example:
Xirona Golden Sky, Merck, Silica, CI 77891 (Titanium Dioxide), Tin Oxide,
Xirona Caribbean Blue, Merck, Mica, CI 77891 (Titanium Dioxide), Silica, Tin Oxide,
Xirona Kiwi Rose, Merck, Silica, CI 77891 (Titanium Dioxide), Tin Oxide,
Xirona Magic Mauve, Merck, Silica, CI 77891 (Titanium Dioxide), Tin Oxide.
In addition, particularly preferred color pigments with the trade name Unipure® are for example:
Unipure Red LC 381 EM, Sensient CI 77491 (Iron Oxides), Silica,
Unipure Black LC 989 EM, Sensient, CI 77499 (Iron Oxides), Silica,
Unipure Yellow LC 182 EM, Sensient, CI 77492 (Iron Oxides), Silica.

In a further embodiment, the composition as contemplated herein may also comprise (a) one or more colorant compounds (a2) from the group consisting of organic pigments.

The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyrrole, indigo, thioindido, dioxazine, and/or triarylmethane compounds.

Examples of organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

In a further embodiment, a process as contemplated herein is exemplified in that the agent (a) contains at least one colorant compound (a2) from the group of organic pigments selected from the group of carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate, or even aluminum.

For example, alizarin color varnish can be used.

Due to their excellent light and temperature resistance, the use of the above pigments in the agent (a) of the process as contemplated herein is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, such as 14 to 30 µm. The mean particle size $D50D_{50}$, for example, can be determined using dynamic light scattering (DLS).

To achieve the highest possible gloss, it has proved particularly advantageous to use the pigments in certain quantity ranges in the medium (a). The pigment or pigments are preferably used in an amount of from about 0.001 to about 20% by weight, more preferably from about 0.1 to about 8% by weight, still more preferably from about 0.6 to about 6% by weight, and very particularly preferably from about 1.0 to about 4.5% by weight, in each case based on the total weight of the agent (a).

In another very particularly preferred embodiment, a process as contemplated herein is exemplified in that the agent (a) contains—based on the total weight of the agent (a)—one or more pigments in a total amount of from about 0.001 to about 20% by weight, more preferably from about 0.1 to about 8% by weight, still more preferably from about 0.3 to about 6% by weight, and very particularly preferably from about 0.5 to about 4.5% by weight.

In a further quite particularly preferred embodiment, a process as contemplated herein is exemplified in that the agent (a) contains—based on the total weight of the agent (a)—one or more inorganic pigments in a total amount of from about 0.001 to about 20% by weight, more preferably from about 0.1 to about 8% by weight, still more preferably from about 0.3 to about 6% by weight, and very particularly preferably from about 0.5 to about 4.5% by weight.

As colorant compounds (a2), the agents (a) used in the process as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes, or indophenols.

The direct dyes within the meaning of the present disclosure have a solubility in water (760 mmHg) at 25° C. of more than 0.5 g/L and are therefore not to be regarded as pigments. Preferably, the direct dyes within the meaning of the present disclosure have a solubility in water (760 mmHg) at 25° C. of more than 1.0 g/L.

Direct dyes can be divided into anionic, cationic, and non-ionic direct dyes.

In a further embodiment, a process as contemplated herein is exemplified in that the agent (a) comprises at least one colorant compound (a2) from the group including anionic, nonionic, and cationic direct dyes.

Suitable cationic direct dyes include Basic Blue 7, Basic Blue 26, HC Blue 16, Basic Violet 2, and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, and Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethyl-amino-4-nitrophenol.

In the course of the work leading to the present disclosure, it has been found that agents (a) containing at least one anionic direct dye (a2) are also suitable.

In a further embodiment, a process as contemplated herein is therefore exemplified in that the agent (a) comprises at least one anionic direct dye.

Anionic direct dyes are also called acid dyes. Acid dyes are direct dyes that have at least one carboxylic acid group (—COOH) and/or one sulphonic acid group (—$SO_3H$). Depending on the pH, the protonated forms (—COOH, —$SO_3H$) of the carboxylic or sulfonic acid moieties are in equilibrium with their deprotonated forms (—COO⁻, —$SO_3$— present). The proportion of protonated forms increases with decreasing pH value. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

Suitable in one embodiment is thus a process for dyeing keratinous material, which is exemplified in that the composition (a) comprises at least one anionic direct dye selected from the group consisting of nitrophenylenediamines, nitroaminophenols, azo dyes, anthraquinone dyes, triarylmethane dyes, xanthene dyes, rhodamine dyes, oxazine dyes and/or indophenol dyes, the xanthene dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—$SO_3H$), a sodium sulfonate group (—$SO_3Na$), and/or a potassium sulfonate group (—$SO_3H$).

As further suitable acid dyes, for example, one or more compounds may be selected from the following group: Acid Yellow 1 (D&C Yellow 7, Citronin A, Ext. D&C Yellow No. 7, Japan Yellow 403,CI 10316, COLIPA n° B001), Acid Yellow 3 (COLIPA n° : C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1;CI 20170; KATSU201; nosodiumsalt; Brown No.201; RESORCIN BROWN; ACID ORANGE 24; Japan Brown 201; D & C Brown No.1), Acid Red 14 (C.I.14720), Acid Red 18 (E124, Red 18; CI 16255), Acid Red 27 (E 123, CI 16185, C-Rot 46, Echtrot D, FD&C Red Nr.2, Food Red 9, Naphtholrot S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C53, CI 45410), Acid Red 95 (CI 45425, Erythrosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

For example, the water solubility of anionic direct dyes can be determined in the following way; 0.1 g of the anionic direct dye is placed in a beaker. A stirrer is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyeazo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high-water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino)phenyl} {4-[(N-ethyl(3-sulfonatobenzyl)imino]-2,5 -cyclohexadien-1-ylidene}methyl)-benzenesulfonate and has a solubility in water of more than 20% by weight (25° C.).

In a further embodiment, a process as contemplated herein is therefore exemplified in that the agent (a) comprises at least one direct dye (a2) selected from the group consisting of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

The direct dye(s) can be used in different amounts in the medium (a), depending on the desired color intensity. Particularly good results could be obtained if the agent (a)—based on the total weight of the agent (a)—contains one or more direct dyes (b) in a total amount of from about 0.01 to about 10.0% by weight, preferably from about 0.1 to about 8.0% by weight, more preferably from about 0.2 to about 6.0% by weight, and most preferably from about 0.5 to about 4.5% by weight.

Furthermore, the agent (a) may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (thermochromism).

The agent (a) may contain—based on the total weight of the agent (a)—one or more photochromic dyes (b) in a total amount of from about 0.01 to about 10.0% by weight, preferably from about 0.1 to about 8.0% by weight, more preferably from about 0.2 to about 6.0% by weight, and most preferably from about 0.5 to about 4.5% by weight.

The agent (a) may contain—based on the total weight of the agent (a)—one or more thermochromic dyes (b) in a total amount of from about 0.01 to about 10.0% by weight, preferably from about 0.1 to about 8.0% by weight, more preferably from about 0.2 to about 6.0% by weight, and very preferably from about 0.5 to about 4.5% by weight Nonionic Surfactants (a3) in the Medium (a)

As a third ingredient (a3) essential to the present disclosure, the composition (a) contains at least one nonionic surfactant. It has been shown that the use of nonionic surfactants enhances the gloss that can be produced by processes as contemplated herein in a synergistic manner Non-ionic surfactants (Tnio) contain as hydrophilic group, for example, a polyol group, a polyalkylene glycol ether group, or a combination of polyol and polyglycol ether group. Such links include:

addition products of 2 to 50 mol ethylene oxide and/or 0 to 5 mol propylene oxide to linear and branched fatty alcohols with 6 to 30 C atoms, the fatty alcohol polyglycol ethers or the fatty alcohol polypropylene glycol ethers or mixed fatty alcohol polyethers, addition products of 2 to 50 mol ethylene oxide and/or 0 to 5 mol propylene oxide to linear and branched fatty acids with 6 to 30 C atoms, the fatty acid polyglycol ethers or the fatty acid polypropylene glycol ethers or mixed fatty acid polyethers, addition products of 2 to 50 mol ethylene oxide and/or 0 to 5 mol propylene oxide to linear and branched alkylphenols having 8 to 15 C atoms in the alkyl group, the alkylphenol polyglycol ethers or the alkylpropylene glycol ethers or mixed alkylphenol polyethers, with a methyl or $C_2$-$C_6$-alkyl radical end-group capped addition products of 2 to 50 moles of ethylene oxide and/or 0 to 5 moles of propylene oxide to linear and branched fatty alcohols with 8 to 30 C atoms, to fatty acids with 8 to 30 C atoms and to alkylphenols with 8 to 15 C atoms in the alkyl group, such as the grades available under the sales names Dehydol® LS, Dehydol® LT (Cognis), $C_{12}$-$C_{30}$ fatty acid mono- and diesters of addition products of 1 to 30 mol ethylene oxide to glycerol, addition products of 5 to 60 mol ethylene oxide to castor oil and hardened castor oil, polyol fatty acid esters, such as the commercial product Hydagen® HSP (Cognis) or Sovermol® types (Cognis), alkoxylated triglycerides, alkoxylated fatty acid alkyl esters of the formula (Tnio-1)

$$R^1CO—(OCH_2CHR^2)_w OR^3 \qquad \text{(Tnio-1)}$$

in which $R^1CO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms and w is a number from 1 to 20, amine oxides, hydroxy mixed ethers, as described for example in DE-OS 19738866, sorbitan fatty acid esters and addition products of ethylene oxide to sorbitan fatty acid esters such as polysorbates, sugar fatty acid esters and addition products of ethylene oxide to sugar fatty acid ester, addition products of ethylene oxide to fatty acid alkanolamides and fatty amines, sugar tensides of the alkyl and alkenyl oligoglycosides type according to formula (E4-II), $$R^4O—[G]_p \qquad \text{(Tnio-2)}$$

in which $R^4$ is an alkyl or alkenyl radical containing 4 to 22 carbon atoms, G is a sugar residue containing 5 or 6 carbon atoms and p is several 1 to 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e., the distribution of mono- and oligoglycosides and stands for a number between 1 and 10. While p must always be an integer in the individual molecule and can assume the values p=1 to 6, the value p for a certain alkyl oligoglycosides is an analytically determined arithmetical quantity, which usually represents a fractional number. Preferably alkyl and/or alkenyl oligoglycosides with an average degree of oligomerization p of 1.1 to 3.0 are used. From an application technology point of view, those alkyl and/or alkenyl oligoglycosides are preferred whose degree of oligomerization is less than 1.7 and lies between 1.2 and 1.4. The alkyl or alkenyl radical $R^4$ can be derived from primary alcohols containing 4 to 11, preferably 8 to 10, carbon atoms. Typical examples are butanol, caproic alcohol, caprylic alcohol, caprin alcohol, and undecrylic alcohol, as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than 6% by weight of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and their technical mixtures, which can be obtained as described above. Preferred are alkyl oligoglucosides based on hardened $C_{12/14}$-coconut alcohol with a DP of 1 to 3.

sugar surfactants of the fatty acid N-alkyl polyhydroxyalkylamide type, a nonionic surfactant of formula (Tnio-3)

$$R^5CO—NR^6— \qquad \text{(Tnio-3)}$$

in which $R^5CO$ is an aliphatic acyl radical containing 6 to 22 carbon atoms, $R^6$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO—(NR^8)—CH_2—[CH(OH)]_4—CH_2OH \qquad \text{(Tnio-4).}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid, or erucic acid, or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The selection of certain non-ionic surfactants has proven to be particularly advantageous, as these enhance the gloss to a special degree. Very preferably, the agent (a) contains at least one highly ethoxylated fatty alcohol, i.e., a fatty alcohol with a degree of ethoxylation of 80 to 120.

In a further preferred embodiment, a process as contemplated herein is exemplified in that the agent (a) comprises at least one ethoxylated $C_8$-$C_{24}$ fatty alcohol (a3) having a degree of ethoxylation of 80 to 120.

As contemplated herein, fatty alcohols are to be understood as saturated or unsaturated, unbranched or branched, $C_8$-$C_{24}$ alkyl groups with hydroxy substitution. Unsaturated fatty alcohols can be monounsaturated or polyunsaturated. In the case of an unsaturated fatty alcohol, its C—C double bond(s) may have the cis or trans configuration.

Preferred fatty alcohols are octan-1-ol (octyl alcohol, caprylic alcohol), decan-1-ol (decyl alcohol, caprylic alcohol), dodecan-1-ol (dodecyl alcohol, lauryl alcohol), tetradecan-1-ol, (tetradecyl alcohol, myristyl alcohol), hexadecan-1-ol (hexadecyl alcohol, cetyl alcohol, palmityl alcohol), Octadecan-1-ol (octadecyl alcohol, stearyl alcohol), (9Z)-octadec-9-en-1-ol (oleyl alcohol), (9E)-octadec-9-en-1-ol (elaidyl alcohol), (9Z, 12Z)-octadeca-9,12-dien-1-ol (linoleyl alcohol), (9Z,12Z,15Z)-octadeca-9,12,15-trien-1-ol (linolenoyl alcohol), eicosan-1-ol (eicosyl alcohol, Arachyl alcohol), (9Z)-Eicos-9-en-1-ol (Gadoleyl alcohol), (5Z, 8Z,11Z,14Z)-Eicosa-5,8,11,14-tetraen-1-ol (Arachidone alcohol), Docosan-1-ol (docosyl alcohol, behenyl alcohol), (13E)-docosen-1-ol (brassidyl alcohol) and (13Z)-docos-13-en-1-ol (erucyl alcohol). Within this group, hexadecan-1-ol (hexadecyl alcohol, cetyl alcohol, palmityl alcohol), and octadecan-1-ol (octadecyl alcohol, stearyl alcohol) are particularly preferred fatty alcohols.

These fatty alcohols ethoxylated with a degree of ethoxylation of 80 to 120. Ethoxylation (also oxyethylation) is the reaction of fatty alcohols with ethylene oxide (EO). Insertion of 80 to 120 groupings of the —$CH_2$—$CH_2$—O— type per fatty alcohol molecule results in linear polyethers bearing a hydroxy group at one chain end and the $C_8$-C24 alkyl group of the fatty alcohol at the other chain end.

Preferred highly ethoxylated fatty alcohols (a3) have a degree of ethoxylation of 90 to 110. It is particularly preferred to use ethoxylated fatty alcohols (a3) which have a degree of ethoxylation of 100.

In another very particularly preferred embodiment, a process as contemplated herein is therefore exemplified in that the agent (a) comprises at least one ethoxylated fatty alcohol (a3) of the formula (T-I),

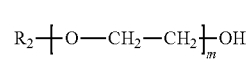

(T-I)

wherein R1 represents a saturated or unsaturated, straight, or branched $C_8$-$C_{24}$ alkyl group, preferably a saturated, straight $C_{16}$- or $C_{18}$ alkyl group, and n is an integer from 80 to 120, preferably an integer from 90 to 110, more preferably an integer from 95 to 105, and particularly preferably the number 100.

In addition, it has been shown to be particularly preferred if the agent (a) also contains a low-ethoxy fatty alcohol, i.e., a fatty alcohol with a degree of ethoxylation of 10 to 40.

In another very particularly preferred embodiment, a process as contemplated herein is therefore exemplified in that the agent (a) comprises at least one ethoxylated $C_8$-$C_{24}$ fatty alcohol (a3) having a degree of ethoxylation of from 10 to 40.

Preferred fatty alcohols are analogously octan-1-ol (octyl alcohol, caprylic alcohol), decan-1-ol (decyl alcohol, capric alcohol), dodecan-1-ol (dodecyl alcohol, lauryl alcohol), tetradecan-1-ol, (tetradecyl alcohol, Myristyl alcohol), Hexadecan-1-ol (Hexadecyl alcohol, Cetyl alcohol, Palmityl alcohol), Octadecan-1-ol (Octadecyl alcohol, Stearyl alcohol), (9Z)-Octadec-9-en-1-ol (Oleyl alcohol), (9E)-Octadec-9-en-1-ol (Elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), eicosan-1-ol (eicosyl alcohol, arachyl alcohol), (9Z)-eicos-9-en-1-ol (gadoleyl alcohol), (5Z,8Z,11Z,14Z)-Eicosa-5,8,11,14-tetraen-1-ol (arachidone alcohol), docosan-1-ol (docosyl alcohol, behenyl alcohol), (13E)-docosen-1-ol (brassidyl alcohol), and (13Z)-docos-13-en-1-ol (erucyl alcohol). Within this group, hexadecan-1-ol (hexadecyl alcohol, cetyl alcohol, palmityl alcohol), and octadecan-1-ol (octadecyl alcohol, stearyl alcohol) are particularly preferred fatty alcohols.

These fatty alcohols ethoxylated with a degree of ethoxylation of 10 to 40. Ethoxylation (also oxyethylation) is the reaction of fatty alcohols with ethylene oxide (EO). Insertion of 10 to 40 groupings of the —CH2—CH2—O— type per fatty alcohol molecule results in linear polyethers bearing a hydroxy group at one chain end and the $C_8$-$C_{24}$ alkyl group of the fatty alcohol at the other chain end.

Preferred low-ethoxylated fatty alcohols (a3) have a degree of ethoxylation of 12 to 30.

In another very particularly preferred embodiment, a process as contemplated herein is therefore exemplified in that the agent (a) comprises at least one ethoxylated fatty alcohol (a3) of the formula (T-II),

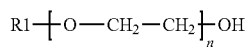

(T-II)

wherein R2 represents a saturated or unsaturated, straight or branched, $C_8$-$C_{24}$ alkyl group, preferably a saturated, straight $C_{16}$- or $C_{18}$ alkyl group, and m is an integer from 10 to 40, preferably an integer from 12 to 30.

It has proved particularly effective to use both a highly ethoxylated $C_8$-$C_{24}$ fatty alcohol and a low-ethoxylated $C_8$-$C_{24}$ fatty alcohol as nonionic surfactants (a3) in agent (a).

The alkylene oxide addition products to fatty acids, each with 2 to 30 moles of ethylene oxide per mole of fatty alcohol or fatty acid, and the sugar surfactants have also proved to be suitable nonionic surfactants. Preparations with excellent properties are also obtained if they contain fatty acid esters of ethoxylated glycerol as non-ionic surfactants.

These connections are identified by the following parameters. The alkyl radical R contains 6 to 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl, and 1-stearyl. Especially preferred are 1-octyl, 1-decyl, 1-lauryl, and 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Non-ionic surfactants have also proved useful as additives for further improving the skin feel during and after application, and their additional use in the preparation of the compositions as contemplated herein can therefore be recommended. Particularly preferred are therefore compositions as contemplated herein with an additional content of about 0.1—about 20 wt. % of nonionic surfactants with an HLB value of about 2—about 18. Such products can be prepared by addition of ethylene oxide to, for example, fatty alcohols with 6-30 C atoms, fatty acids with 6-30 C atoms, glycerol, sorbitan fatty acid partial esters based on $C_{12}$-$C_{18}$ fatty acids, or fatty acid alkanolamides. The HLB value means the proportion of hydrophilic groups, e.g., glycol ether or polyol groups, relative to the total molecule and is calculated according to the relationship $$HLB=\tfrac{1}{5}\times(100 \text{ wt.-\% L}),$$

where % by weight L is the weight fraction of lipophilic groups, e.g., alkyl or acyl groups with 6-30 C atoms in the surfactant molecule.

In the course of the work leading to the present disclosure it has been found that the use of nonionic surfactants improves the gloss of dyed keratin materials. Other nonionic ingredients have also been shown to be beneficial in this regard. It has been shown that the higher the proportion of non-ionic components in the average (a), the higher the gloss.

It has proved particularly preferable in this connection if the proportion by weight of all nonionic components in the formulation (a)—based on the total weight of the formulation (a)—is 80% by weight, preferably 85% by weight, more preferably 90% by weight, and very particularly preferably 99% by weight. In other words, in the context of this embodiment, the agent (a) includes 80% by weight, preferably 85% by weight, further preferably 90% by weight, and most preferably 99% by weight, of nonionic ingredients.

In another particularly preferred embodiment, a process as contemplated herein is exemplified in that the proportion by weight of all nonionic constituents in the composition (a)—based on the total weight of the composition (a)—is at least 80% by weight, preferably at least 85% by weight, further preferably at least 90% by weight, and very particularly preferably at least 98% by weight.

In other words, the process as contemplated herein of this particularly preferred embodiment is exemplified in that the summed weight fraction of all nonionic constituents contained in the composition (a)—based on the total weight of the composition (a)—is at least 80% by weight, preferably at least 85% by weight, further preferably at least 90% by weight, and very particularly preferably at least 98% by weight.

Example: Contains 100 g of an Agent (a)
10 g cetearyl alcohol (non-ionic fatty ingredient)
5.0 g Paraffinum Liquidum (non-ionic fat ingredient)
1.5 g Ceteareth-30 (non-ionic surfactant)
0.5 g Ceteareth-100 (non-ionic surfactant)
2.0 g pearlescent pigment (non-ionic pigment)
2.0 g ethanol (non-ionic solvent)
2.0 g aminosilicone (non-ionic aminosilicone)
ad 100 g water (non-ionic solvent)
The weight percentage of all nonionic constituents—based on the total weight of the formulation (a)—is 100 wt. %.

Example: Contains 100 g of an Agent (a)
15 g cetearyl alcohol (non-ionic fatty ingredient)
10.0 g Paraffinum Liquidum (non-ionic fat ingredient)
2.5 g Ceteareth-30 (non-ionic surfactant)
1.5 g Ceteareth-100 (non-ionic surfactant)
1.5 g pearlescent pigment (non-ionic pigment)
6.0 g Phenoxyethanol (non-ionic solvent)
2.0 g aminosilicone (non-ionic aminosilicone)
0.5 g sodium hydroxide (salt, ionic)
ad 100 g water (non-ionic solvent)
The weight percentage of all nonionic constituents—based on the total weight of the formulation (a)—is 99.5 wt. %.

pH Value of the Agent (a)

The colorant (a) is preferably adjusted to a neutral to alkaline pH value. Very preferably, the colorant (a) is adjusted to an alkaline pH value. Under basic conditions, the amino-functionalized silicone polymer (a1) can be dissolved or dispersed particularly well and without protonation.

To adjust the desired pH, the agent (a) preferably contains at least one alkalizing agent. The pH values for the purposes of the present disclosure are pH values measured at a temperature of 22° C.

As alkalizing agent, agent (a) may contain, for example, ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore exemplified in that the agent as contemplated herein contains an alkanolamine selected from 2-aminoethan-1-ol and/or 2-amino-2-methylpropan-1-ol as alkalizing agent.

A particularly preferred embodiment is therefore exemplified in that the agent as contemplated herein contains an alkanolamine selected from 2-aminoethan-1-ol and/or 2-amino-2-methylpropan-1-ol as alkalizing agent. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate, and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate, and potassium carbonate.

In another very particularly preferred embodiment, a process as contemplated herein is exemplified in that the colorant (a) comprises at least one alkalizing agent selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate, and potassium carbonate.

Particularly good results were obtained when the agent (a) was adjusted to a pH of about 7.0 to about 11.5 preferably from about 8.0 to about 11.0, and especially preferably from about 8.5 to about 10.5.

In another very particularly preferred embodiment, a process as contemplated herein is exemplified in that the agent (a) comprises water and has a pH value of from about 7.0 to about 11.5, preferably from about 8.0 to about 11.0, and particularly preferably from about 8.5 to about 10.5.

Acid (b1) on Agent (b)

Following the application of the coloring agent (a) on the keratin material, the post-treatment agent (b) is applied. The aftertreatment agent (b) is an acid-adjusted solution, dispersion, or emulsion. As an ingredient essential to the present disclosure, the aftertreatment agent (b) therefore contains at least one acid (b1)

Certain acids have proven to be particularly suitable for adjusting the desired pH value. These acids may be selected, for example, from the group including citric acid, tartaric acid, malic acid, lactic acid, acetic acid, methanesulfonic acid, benzoic acid, malonic acid, oxalic acid, 1-hydroxyethane-1,1-diphosphonic acid, sulfuric acid, hydrochloric acid, and phosphoric acid.

In another very particularly preferred embodiment, a process as contemplated herein is exemplified in that the agent (b) comprises at least one acid (b1) selected from the group including citric acid, tartaric acid, malic acid, lactic acid, acetic acid, methanesulfonic acid, benzoic acid, malonic acid, oxalic acid, 1-hydroxyethane-1,1-diphosphonic acid, sulfuric acid, hydrochloric acid, and phosphoric acid.

As soon as the aftertreatment agent (b) is applied, it meets the amino silicones (a1), and colorant compounds (a2) deposited on the keratin material. Since the agent (b) is acidic, it also lowers the pH in the immediate vicinity of the aminosilicone (a1). In this context, it is assumed that the reduction in pH results in a protonation of the previously uncharged aminosilicone (a1), because of which adhesion forces to the keratin material are further strengthened and the colorant compounds (a2) are bound even more strongly to the hair. This massively improves the wash fastness of the resulting coloration while preserving the hair's shine. For this reason, the aftertreatment agent (b) is preferably adjusted to an acidic pH in the range from about 1.5 to about 5.5 preferably from about 2.0 to about 4.8, and particularly preferably from about 2.5 to about 4.5.

In another very particularly preferred embodiment, a process as contemplated herein is exemplified in that the agent (b) comprises water and has a pH of from about 1.5 to about 5.5 preferably from about 2.0 to about 4.8, and particularly preferably from about 2.5 to about 4.5.

In the course of the work leading to the present disclosure, the choice of the time at which the pH is lowered has been found to be essential to produce stable layers on the keratin material. It is essential to the present disclosure that the pH of the aminosilicone (a1) is lowered after it has been applied to the keratin fiber. When aminosilicone (a1) and acid are applied simultaneously, there is no significant enhancement of binding to keratin. For this reason, it is essential to the present disclosure to incorporate the acid (b1) into the aftertreatment agent (b).

It was found that the more the pH was lowered in the vicinity of the aminosilicone (a1), the greater the improvement in wash fastness. In other words, the colorations were particularly stable when the colorant (a) was comparatively strongly alkaline and the aftertreatment agent (b) had a relatively acidic pH value.

Other Ingredients in Products (a) and (b)

The agents (a) and (b) described above may also contain one or more optional ingredients.

For agent (a), the nonionic ingredients are particularly preferably selected from those listed below.

The agents (b) may additionally contain one or more surfactants. The term surfactants refer to surface-active substances. A distinction is made between anionic surfactants consisting of a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

The term zwitterionic surfactants is used to describe surface-active compounds that carry at least one quaternary ammonium group and at least one $—COO^{(-)}$ or $—SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate.

A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino propionates, aminoglycinate, imidazoliniumbetaines, and sulfobetaines.

Particularly preferred ampholytic surfactants are N-cocoalkylaminopropionate, cocoacylaminoethylaminopropionate and $C_{12}$-$C_{18}$ acylsarcosine.

The agents (b) may also additionally contain at least one nonionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide. The non-ionic surfactants are used in a total quantity of about 0.1 to about 45% by weight, preferably from about 1 to about 30% by weight, and very preferably from about 1 to about 15% by weight-based on the total weight of the respective agent.

Furthermore, the agents (b) may also additionally comprise at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are:
quaternary ammonium compounds which, as hydrophobic radicals, may carry one or two alkyl chains with a chain length of 8 to 28 C atoms,
quaternary phosphonium salts substituted with one or more alkyl chains with a chain length of 8 to 28 C atoms, or
tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of about 0.1 to about 45 wt. %, preferably from about 1 to about 30 wt. %, and most preferably from about 1 to about 15 wt. %—based on the total weight of the respective agent.

Furthermore, the compositions (b) as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of about 0.1 to about 45 wt. %, preferably from about 1 to about 30 wt. %, and most preferably from about 1 to about 15 wt. %—based on the total weight of the respective agent.

The agents may also contain other active ingredients, auxiliaries and additives, such as solvents; fatty ingredients such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; polymers; structurants such as glucose, maleic acid and lactic acid, hair conditioning compounds such as phospholipids, for example lecitin and kephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$, and air.

The selection of these other substances will be made by the specialist according to the desired properties of the agents. About other optional components and the quantities of these components used, explicit reference is made to the relevant manuals known to the specialist. The additional active ingredients and auxiliary substances are preferably used in the preparations as contemplated herein in quantities of about 0.0001 to about 25 wt. % each, such as about 0.0005 to about 15 wt. %, based on the total weight of the respective agent.

Process for Dyeing Keratin Materials

In the procedure as contemplated herein, agents (a) and (b) are applied to the keratinous materials, to human hair. Agent (b) is an after-treatment agent and is therefore applied after dyeing agent (a).

Therefore, a method for dyeing keratinous material, in particular human hair, comprising the following steps in the order given is particularly preferred:
in a first step, applying a coloring agent (a) to the keratinous material, said agent (a) comprising:
(a1) at least one amino-functionalized silicone polymer,
(a2) at least one color-imparting compound, and
(a3) at least one nonionic surfactant, and
in a second step, applying a post-treatment agent (b) to the keratinous material, the agent comprising (b):
(b1) at least one acid.

The agents (a) and (b) are particularly preferably applied within one and the same dyeing process, which means that there is a period of a maximum of several hours between the application of agents (a) and (b).

In a further preferred embodiment, a method as contemplated herein is exemplified in that first the agent (a) is applied, and then the agent (b) is applied, the time between the application of the agents (a) and (b) being at most 24 hours, preferably at most 12 hours, and particularly preferably at most 6 hours.

In the process as contemplated herein, the keratin materials, in particular human hair, are first treated with colorant (a). Subsequently, the aftertreatment agent (b) is applied to the keratin materials, which lowers the pH value on the surface of the keratin material, thus fixing or immobilizing the active ingredients contained in the agent (a) on the keratin. Preferably, the agent (b) itself does not contain any dyes or color-imparting compounds.

The technical application properties of the resulting dyeing can be further improved by selecting the optimum process conditions.

In the context of a further form of execution, a procedure comprising the following steps in the order indicated is particularly preferred
(1) apply the staining agent (a) on the keratinous material,
(2) allow the agent (a) to act for a period of 10 seconds to 10 minutes, preferably from 10 seconds to 5 minutes,
(3) if necessary, rinse the keratinous material with water,
(4) apply the after-treatment agent (b) on the keratinous material,
(5) allow the agent (b) to act for a period of 30 seconds to 30 minutes, preferably from 30 seconds to 10 minutes, and
(6) rinse the keratinous material with water.

The rinsing of the keratinous material with water in steps (3) and (6) of the process is understood, as contemplated herein, to mean that only water is used for the rinsing process, without any other agents other than agents (a) and (b).

In a first step (1), agent (a) is applied to the keratin materials, especially human hair.

After application, the agent (a) can act on the keratin materials. The process as contemplated herein permits the production of dyes with particularly good intensity and wash fastness even with a short contact time of the agent (a). In this context, application times from 10 seconds to 10 minutes, preferably from 20 seconds to 5 minutes, and especially preferably from 30 seconds to 2 minutes, on the hair have proven to be particularly beneficial.

In a preferred embodiment of the method as contemplated herein, the agent (a) can now be rinsed from the keratin materials before the agent (b) is applied to the hair in the subsequent step.

Particularly intense and glossy colorations were obtained when agent (b) was applied to the keratin materials that were still exposed to agent (a).

In step (4), agent (b) is now applied to the keratin materials. After application, let the agent (b) act on the hair.

The process as contemplated herein permits the production of colorations with particularly good intensity and high gloss even with a short reaction time of the agent (b). Application times from about 10 seconds to about 10 minutes, preferably from about 20 seconds to about 5 minutes, and most preferably from about 30 seconds to about 3 minutes, on the hair have proven to be particularly beneficial.

In step (6), agent (b) (and any remaining agent (a)) is rinsed out of the keratin material with water.

In the context of a further form of execution, a procedure comprising the following steps in the order indicated is particularly preferred (1) apply agent (a) on the keratinous material,
(2) allow the agent (a) to act for a period of about 10 seconds to about 10 minutes, preferably from about 10 seconds to about 5 minutes,
(3) do not rinse,
(4) apply agent (b) on the keratinous material,
(5) allow the agent (b) to act for a period of about 30 seconds to about 30 minutes, preferably from about 30 seconds to about 10 minutes, and
(6) rinse the keratinous material with water.

In this embodiment, the sequence of steps (1) to (6) preferably takes place within 24 hours.

Multi-Component Packaging Unit (Kit-of-Parts)

To increase user comfort, the user is preferably provided with all required resources in the form of a multi-component packaging unit (kit-of-parts).

A second subject of the present disclosure is therefore a multi-component packaging unit (kit-of-parts) for coloring keratinous material, comprehensively packaged separately from one another:
 a first container containing a coloring agent (a), said agent containing (a):
  (a1) at least one amino-functionalized silicone polymer,
  (a2) at least one color-imparting compound, and
  (a3) at least one nonionic surfactant, and
 a second container containing an agent (b), wherein the agent contains (b):
  (b1) at least one acid,
wherein the ingredients (a1), (a2), (a3), and (b1) have already been disclosed in detail in the description of the first subject matter of the present disclosure.

The amino-functionalized silicone polymers (a1) contained in agent (a) of the kit correspond to the amino-functionalized silicone polymers (a1) that were also used in agent (a) of the previously described process.

The colorant compounds (a2) contained in the agent (a) of the kit correspond to the colorant compounds (a2) that were also used in the agent (a) of the previously described process.

The nonionic surfactants (a3) optionally contained in the agent (a) of the kit correspond to the nonionic surfactants (a3) also used in the agent (a) of the previously described process.

The acids (b1) contained in the agent (b) of the kit correspond to the acids (b1) that were also used in the agent (b) of the previously described process.

With respect to the other preferred embodiments of the multi-component packaging unit as contemplated herein, the same applies mutatis mutandis to the procedure as contemplated herein.

EXAMPLES

1. Formulations

The following formulations were prepared (all figures are in wt % unless otherwise stated).

Dyeing Agent (a)

| | | Agent (aE) |
|---|---|---|
| Cetyl alcohol | nonionic | 3.6 |
| Stearyl alcohol | nonionic | 2.0 |
| Paraffinum Liquidum | nonionic | 2.1 |
| Eumulgin B3 (C16-C18 fatty alcohols, ethoxylated 30 EO, ceteareth-30), CAS No 68439-49-6 | nonionic | 1.2 |

-continued

| | | Agent (aE) |
|---|---|---|
| Slurry 100 (Stearyl alcohol, ethoxylated 100 EO) CAS-No. 9005-00-9 | nonionic | 0.6 |
| Glyceryl stearate | nonionic | 0.6 |
| 1.2-propanediol | nonionic | 6.0 |
| Dow Corning 2-8566 (Siloxanes and Silicones, 3-[(2-Aminoethyl)amino]-2-methylpropyl Me, Di-Me-Siloxane" | nonionic | 2.0 |
| Colorona Bronze (Mica, CI77491 Iron oxides) | nonionic | 2.0 |
| Water | nonionic | ad 100 |

After-Treatment Agent (b)

| Agent (b) | (bE) present disclosure |
|---|---|
| Citric acid | ad pH 3.0 |
| Water | ad 100 |

2. Application

Compound (a) was applied to a strand of hair (Kerling, Euronatural hair white, liquor ratio: 4 g of agent (a) per g of hair strand) applied and then left to act for one minute. The hair strand was then dipped into the post-treatment agent (b) and left in it for 1 minute. Subsequently, each hair strand was thoroughly washed (1 minute) with water, dried, and visually evaluated under the daylight lamp.

To determine wash fastness, previously dyed hair strands were placed in an ultrasonic bath filled with a 1% solution of a commercial shampoo (foams, 7 herbs). Then the hair strands were treated with ultrasound according to a standardized procedure corresponding to 6 hair washes. After this period, the strands were removed from the ultrasonic bath, dried, and visually assessed again under the daylight lamp.

To determine wash fastness, previously dyed hair strands were placed in an ultrasonic bath filled with a 1% solution of a commercial shampoo (Schauma, 7 herbs). Then the hair strands were treated with ultrasound according to a standardized procedure corresponding to 3 hair washes. After this period, the strands were removed from the ultrasonic bath, dried, and visually assessed again under the daylight lamp.

| | Application |
|---|---|
| Dyeing agent (a) | (aE) |
| Rinse out agent (a) | no rinsing |
| After-treatment agent (b) | (bE) |
| Color Intensity (directly after staining) | glittering, gold bronze +++ |
| Hair gloss | +++ |
| Hair shine after 3 hair washes | +++ |

Color intensity: − = uncolored,
+ = low,
++ = average,
+++ = exceptionally good

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material, comprising:
applying a coloring agent (a) to the keratinous material, the agent (a) comprising:
(a1) at least one amino-functionalized silicone polymer,
(a2) at least one color-imparting compound, and
(a3) at least one nonionic surfactant; and
applying a post-treatment agent (b) to the keratinous material, the agent (b) comprising:
(b 1) at least one acid.

2. The process according to claim 1, wherein the agent (a) comprises at least one amino-functionalized silicone polymer (a1) having at least one secondary amino group.

3. The process according to claim 1, wherein the agent (a) comprises at least one amino-functionalized silicone polymer (a1) comprising at least one structural unit of the formula (Si amino),

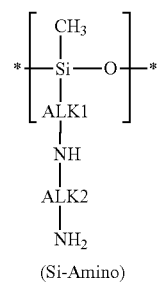

(Si-Amino)

where ALK1 and ALK2 independently of one another represent a linear or branched, divalent $C_1$-$C_{20}$ alkylene group.

4. The process according to claim 1 wherein the agent (a) comprises at least one amino-functionalized silicone polymer (a1) comprising structural units of the formula (Si-I) and of the formula (Si-II)

(Si-I)

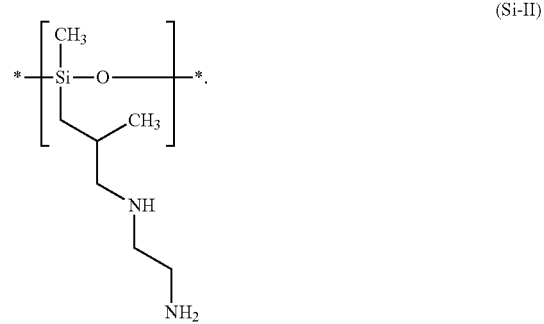
(Si-II)

5. The process according to claim 1 wherein the agent (a) contains—based on the total weight of the agent (a)—one or more amino-functionalized silicone polymers (a1) in a total amount of from about 0.1 to about 8.0% by weight.

6. The process according to claim 1 wherein the agent (a) comprises at least one color-imparting compound (a2) from the group consisting of pigments, direct dyes, photochromic dyes, and thermochromic dyes.

7. The process according to claim 1 wherein the agent (a) comprises at least one colorant compound (a2) from the group of inorganic pigments selected from the group of colored metal oxides, metal hydroxides, metal oxide hydrates, silicates, metal sulfides, complex metal cyanides, metal sulfates, and bronze pigments and/or from colored mica- or mica-based pigments coated with at least one metal oxide and/or a metal oxychloride.

8. The process according to claim 1 wherein the composition (a) comprises at least one coloring compound (a2) from the group of pigments selected from mica- or mica-based pigments which are reacted with one or more metal oxides selected from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288), and/or iron blue (ferric ferrocyanide, CI 77510).

9. The process according to claim 1 wherein the agent (a) contains—based on the total weight of the agent (a)—one or more inorganic pigments in a total amount of from about 0.001 to about 20% by weight.

10. The process according to claim 1 wherein the agent (a) comprises at least one ethoxylated $C_8$-C24 fatty alcohol (a3) having a degree of ethoxylation of 80 to 120.

11. The process according to claim 1 wherein the agent (a) comprises at least one ethoxylated fatty alcohol (a3) of formula (T-I),

(T-I)

wherein R1 represents a saturated or unsaturated, straight, or branched $C_8$-C24 alkyl group, and
n is an integer from 80 to 120.

12. The process according to claim 1 wherein the agent (a) comprises at least one ethoxylated fatty alcohol (a3) having a degree of ethoxylation of 10 to 40.

13. The process according to claim 1 wherein the agent (a) comprises at least one ethoxylated fatty alcohol (a3) of formula (T-II),

(T-II)

wherein R2 represents a saturated or unsaturated, straight, or branched $C_8$-$C_{24}$ alkyl group, and m is an integer from 10 to 40.

14. The process according to claim 1 wherein the proportion by weight of all nonionic constituents in the agent (a)—based on the total weight of the agent (a)—is at least 80% by weigh.

15. The process according to claim 1 wherein the agent (a) comprises water and has a pH of from about 7.0 to about 11.5.

16. The process according to claim 1 wherein the agent (b) comprises at least one acid (b1) selected from the group consisting of citric acid, tartaric acid, malic acid, lactic acid, acetic acid, methanesulfonic acid, benzoic acid, malonic acid, oxalic acid, 1-hydroxyethane-1,1-diphosphonic acid, sulfuric acid, hydrochloric acid, and phosphoric acid.

17. The process according to claim 1 wherein the agent (b) comprises water and has a pH of from about 1.5 to about 5.5.

18. The process according to claim 1 wherein first the agent (a) is applied, then the agent (b) is applied, the period between the application of the agents (a) and (b) being at most 24 hours.

19. The process according to claims1 comprising the following steps in the order indicated.
   (1) applying the staining agent (a) on the keratinous material,
   (2) allowing the agent (a) to act for a period of about 10 seconds to about 10 minutes,
   (3) if necessary, rinsing the keratinous material with water,
   (4) applying the after-treatment agent (b) on the keratinous material,
   (5) allowing the agent (b) to act for a period of about 30 seconds to about 30 minutes, and
   (6) rinsing the keratinous material with water.

* * * * *

UNITED STATES PATENT AND TRADEMARK OFFICE
CERTIFICATE OF CORRECTION

| | |
|---|---|
| PATENT NO. | : 11,529,304 B2 |
| APPLICATION NO. | : 17/415625 |
| DATED | : December 20, 2022 |
| INVENTOR(S) | : Costanze Neuba et al. |

It is certified that error appears in the above-identified patent and that said Letters Patent is hereby corrected as shown below:

In the Specification

Column 19, Line 45 change "((4-sulfophenyeazo)" to --((4-sulfophenyl)azo--.
Column 22, Line 24 change "$R^5CO-NR^6$-" to --$R^5CO-NR^6$-[Z]--.
Column 23, Line 33 change "$C_8$-C24" to --$C_8$-$C_{24}$--.

Signed and Sealed this
Twenty-first Day of November, 2023

*Katherine Kelly Vidal*

Katherine Kelly Vidal
*Director of the United States Patent and Trademark Office*